US011160681B2

(12) United States Patent
Strøbech et al.

(10) Patent No.: US 11,160,681 B2
(45) Date of Patent: Nov. 2, 2021

(54) OSTOMY DEVICE

(71) Applicant: Coloplast A/S, Humlebaek (DK)

(72) Inventors: Esben Strøbech, Hoersholm (DK); Anders Grove Sund, Alleroed (DK); Kristoffer Hansen, Naerum (DK); Michael Hansen, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 438 days.

(21) Appl. No.: 15/565,448

(22) PCT Filed: Apr. 8, 2016

(86) PCT No.: PCT/DK2016/050099

§ 371 (c)(1),
(2) Date: Oct. 10, 2017

(87) PCT Pub. No.: WO2016/162038

PCT Pub. Date: Oct. 13, 2016

(65) Prior Publication Data

US 2018/0116859 A1 May 3, 2018

(30) Foreign Application Priority Data

Apr. 10, 2015 (DK) ........................... PA 2015 70210

(51) Int. Cl.
*A61F 5/443* (2006.01)
*A61F 5/445* (2006.01)

(52) U.S. Cl.
CPC .............. *A61F 5/443* (2013.01); *A61F 5/445* (2013.01)

(58) Field of Classification Search
CPC ................................. A61F 5/443; A61F 5/445
See application file for complete search history.

(56) References Cited

U.S. PATENT DOCUMENTS 2,608,542 A 8/1952 Smith et al.
2,608,543 A 8/1952 Wiswell
(Continued)

FOREIGN PATENT DOCUMENTS

AU 07572/83 B2 2/2003
AU 2004203234 A1 9/2004
(Continued)

OTHER PUBLICATIONS

"3M(Trademark) Hi-Tack Transfer Adhesive", Information Sheet, Product No. 1504, published Sep. 2006.
(Continued)

*Primary Examiner* — Adam Marcetich
*Assistant Examiner* — Meagan Ngo
(74) *Attorney, Agent, or Firm* — Coloplast Corp., Coloplast A/S; Nick Baumann

(57) ABSTRACT

Disclosed is an ostomy device with an adhesive wafer for attachment to a skin surface of a user and a collecting bag for collecting output from a stoma. The collecting bag is connected to the adhesive wafer, and the adhesive wafer has a through-going hole for accommodating the stoma of the user. The adhesive wafer includes a backing layer, a first switchable adhesive composition, a second adhesive composition, and a release liner. The first adhesive is contained in a recess in the device. The first switchable adhesive composition comprises a polymer and a switch initiator, and can be switched from a first liquid state to a second adhesive state by activation of the switch initiator.

13 Claims, 2 Drawing Sheets

(56) References Cited

U.S. PATENT DOCUMENTS

| | | | |
|---|---|---|---|
| 3,302,647 A | 2/1967 | Marsan | |
| 3,612,053 A | 10/1971 | Pratt | |
| 4,125,522 A | 11/1978 | Becker | |
| 4,367,732 A | 1/1983 | Poulsen et al. | |
| 4,614,787 A | 9/1986 | Szycher et al. | |
| 4,847,137 A | 7/1989 | Kellen et al. | |
| 5,013,307 A | 5/1991 | Broida | |
| 5,030,665 A | 7/1991 | Lee et al. | |
| 5,087,686 A | 2/1992 | Ansell et al. | |
| 5,124,076 A | 6/1992 | Smuckler | |
| 5,256,447 A | 10/1993 | Oxman et al. | |
| 5,387,450 A | 2/1995 | Stewart | |
| 5,412,035 A | 5/1995 | Schmitt et al. | |
| 5,472,991 A | 12/1995 | Schmitt et al. | |
| 5,486,158 A | 1/1996 | Samuelsen | |
| 5,591,447 A | 1/1997 | Jensen | |
| 5,622,711 A | 4/1997 | Chen | |
| 5,633,010 A | 5/1997 | Chen | |
| 5,643,187 A | 7/1997 | Naestoft et al. | |
| 5,648,167 A | 7/1997 | Peck | |
| 5,648,425 A | 7/1997 | Everaerts et al. | |
| 5,695,837 A | 12/1997 | Everaerts et al. | |
| 5,714,225 A | 2/1998 | Hansen et al. | |
| 5,714,305 A | 2/1998 | Teng et al. | |
| 5,722,965 A | 3/1998 | Kuczynski | |
| 5,800,685 A | 9/1998 | Perrault | |
| 5,814,031 A | 9/1998 | Mooney et al. | |
| 5,853,864 A | 12/1998 | Bunnelle | |
| 5,895,623 A | 4/1999 | Trokhan et al. | |
| 5,922,470 A | 7/1999 | Bracken et al. | |
| 6,060,159 A | 5/2000 | Delgado et al. | |
| 6,068,852 A | 5/2000 | Shah | |
| 6,071,268 A | 6/2000 | Wagner | |
| 6,143,798 A | 11/2000 | Jensen et al. | |
| 6,171,289 B1 | 1/2001 | Millot et al. | |
| 6,184,264 B1 | 2/2001 | Webster | |
| 6,231,872 B1 | 5/2001 | Mooney et al. | |
| 6,342,561 B1 | 1/2002 | Engel et al. | |
| 6,399,672 B1 | 6/2002 | Ceska et al. | |
| 6,451,883 B1 | 9/2002 | Chen et al. | |
| 6,589,222 B1 | 7/2003 | Olsen | |
| 6,602,232 B1 | 8/2003 | Keyes | |
| 6,610,762 B1 | 8/2003 | Webster | |
| 6,624,273 B1 | 9/2003 | Everaerts et al. | |
| 6,635,704 B2 | 10/2003 | Engel et al. | |
| 6,718,212 B2 | 4/2004 | Parry et al. | |
| 6,855,386 B1 | 2/2005 | Daniels et al. | |
| 7,067,601 B2 | 6/2006 | Woods et al. | |
| 7,147,742 B2 | 12/2006 | Kirsten | |
| 7,214,217 B2 | 5/2007 | Pedersen et al. | |
| 7,235,593 B2 | 6/2007 | Crivello | |
| 7,259,190 B2 | 8/2007 | Lykke | |
| 7,396,976 B2 | 7/2008 | Hurwitz et al. | |
| 7,399,800 B2 | 7/2008 | Burch | |
| 7,479,530 B2 | 1/2009 | Hughes et al. | |
| 7,501,133 B2 | 3/2009 | McNally-Heintzelman et al. | |
| 7,767,752 B2 | 8/2010 | Kim et al. | |
| 7,836,914 B2 | 11/2010 | Drott et al. | |
| 7,879,942 B2 | 2/2011 | O'Brien et al. | |
| 7,893,179 B2 | 2/2011 | Anderson et al. | |
| 7,901,532 B2 | 3/2011 | Bain et al. | |
| 7,947,366 B2 | 5/2011 | Ishiwatari et al. | |
| 7,968,188 B2 | 6/2011 | Gilbert | |
| 8,044,234 B2 | 10/2011 | Hadba et al. | |
| 8,101,042 B2 | 1/2012 | Gantner et al. | |
| 8,319,003 B2 | 11/2012 | Olsen et al. | |
| 8,329,976 B2 | 12/2012 | Freiding et al. | |
| 8,404,921 B2 | 3/2013 | Lee et al. | |
| 8,409,703 B2 | 4/2013 | Burch | |
| 8,410,332 B2 | 4/2013 | Burton et al. | |
| 8,414,987 B2 | 4/2013 | Guo et al. | |
| 8,439,884 B2 | 5/2013 | Fabo et al. | |
| 8,507,081 B2 | 8/2013 | Strobech et al. | |
| 8,545,468 B2 | 10/2013 | Fabo et al. | |
| 8,557,378 B2 | 10/2013 | Yamanaka et al. | |
| 8,664,326 B2 | 3/2014 | Lee et al. | |
| 8,679,082 B2 | 3/2014 | Bach et al. | |
| 8,697,932 B2 | 4/2014 | Tunius | |
| 8,728,047 B2 | 5/2014 | Ciok | |
| 8,802,806 B2 | 8/2014 | Lam et al. | |
| 8,828,181 B2 | 9/2014 | Burch | |
| 8,864,493 B2 | 10/2014 | Leslie-Martin et al. | |
| 8,951,237 B2 | 2/2015 | Nordby et al. | |
| 8,957,277 B2 | 2/2015 | Carty et al. | |
| 9,023,249 B2 | 5/2015 | Fathi et al. | |
| 9,034,941 B2 | 5/2015 | Nielsen et al. | |
| 9,040,076 B2 | 5/2015 | Tunius | |
| 2002/0128614 A1 | 9/2002 | Cinelli et al. | |
| 2002/0165477 A1 | 11/2002 | Dunshee | |
| 2003/0093042 A1 | 5/2003 | Leisner et al. | |
| 2004/0121120 A1 | 6/2004 | Gray et al. | |
| 2004/0151902 A1* | 8/2004 | Ansell | C08F 277/00 428/343 |
| 2004/0242770 A1 | 12/2004 | Feldstein et al. | |
| 2005/0112182 A1 | 5/2005 | Minami et al. | |
| 2005/0233149 A1 | 10/2005 | Ansell | |
| 2006/0052478 A1 | 3/2006 | Madsen et al. | |
| 2006/0100299 A1 | 5/2006 | Malik et al. | |
| 2006/0200101 A1 | 9/2006 | Mullejans et al. | |
| 2006/0228318 A1 | 10/2006 | Fabo | |
| 2006/0235149 A1 | 10/2006 | Burch | |
| 2007/0004896 A1 | 1/2007 | Ito et al. | |
| 2007/0092733 A1 | 4/2007 | Yang | |
| 2007/0123832 A1 | 5/2007 | Cline et al. | |
| 2007/0191517 A1 | 8/2007 | Chun et al. | |
| 2007/0196454 A1 | 8/2007 | Stockman et al. | |
| 2007/0196455 A1 | 8/2007 | Kamiyama et al. | |
| 2007/0202245 A1 | 8/2007 | Gantner et al. | |
| 2007/0249484 A1 | 10/2007 | Benkhoff et al. | |
| 2007/0255402 A1 | 11/2007 | Moore et al. | |
| 2007/0282284 A1 | 12/2007 | Mullejans et al. | |
| 2008/0097361 A1* | 4/2008 | Fabo | A61F 5/443 604/338 |
| 2009/0012208 A1 | 1/2009 | Madsen et al. | |
| 2009/0171258 A1 | 7/2009 | Stroebeck et al. | |
| 2009/0312685 A1 | 12/2009 | Olsen et al. | |
| 2010/0113999 A1 | 5/2010 | Lam et al. | |
| 2010/0114044 A1 | 5/2010 | Cramer et al. | |
| 2010/0168633 A1 | 7/2010 | Bougherara et al. | |
| 2010/0191201 A1 | 7/2010 | Bach et al. | |
| 2010/0191204 A1 | 7/2010 | Bach et al. | |
| 2010/0198176 A1 | 8/2010 | Stroebech et al. | |
| 2010/0204556 A1 | 8/2010 | Blakley et al. | |
| 2010/0204664 A1 | 8/2010 | Bach et al. | |
| 2010/0204665 A1* | 8/2010 | Stroebech | A61F 5/443 604/344 |
| 2010/0255239 A1 | 10/2010 | Hammond et al. | |
| 2010/0267302 A1 | 10/2010 | Kantner et al. | |
| 2010/0294344 A1 | 11/2010 | Huang | |
| 2010/0324511 A1 | 12/2010 | Dove et al. | |
| 2011/0034890 A1 | 2/2011 | Stroebech et al. | |
| 2011/0045056 A1 | 2/2011 | Munro et al. | |
| 2011/0086077 A1 | 4/2011 | McCrea et al. | |
| 2011/0098665 A1 | 4/2011 | Bach et al. | |
| 2011/0118363 A1 | 5/2011 | Jensen et al. | |
| 2011/0123800 A1 | 5/2011 | Sherman et al. | |
| 2011/0142907 A1 | 6/2011 | Marchitto et al. | |
| 2011/0177329 A1 | 7/2011 | Xia et al. | |
| 2011/0218507 A1 | 9/2011 | Andersen et al. | |
| 2011/0224593 A1 | 9/2011 | Tunius | |
| 2011/0251542 A1 | 10/2011 | Buus et al. | |
| 2011/0278797 A1 | 11/2011 | Moore | |
| 2012/0029455 A1 | 2/2012 | Perez-Foullerat et al. | |
| 2012/0100039 A1 | 4/2012 | Appeaning et al. | |
| 2012/0100326 A1 | 4/2012 | Sherman et al. | |
| 2012/0123220 A1 | 5/2012 | Iyer et al. | |
| 2012/0135225 A1 | 5/2012 | Colas et al. | |
| 2012/0143154 A1 | 6/2012 | Edvardsen et al. | |
| 2012/0143155 A1 | 6/2012 | Edvardsen et al. | |
| 2012/0302844 A1 | 11/2012 | Schnidrig et al. | |
| 2012/0315601 A1 | 12/2012 | Shchori et al. | |
| 2012/0321819 A1 | 12/2012 | Kim et al. | |
| 2013/0004749 A1 | 1/2013 | Hao et al. | |

(56) References Cited

U.S. PATENT DOCUMENTS

| | | | | |
|---|---|---|---|---|
| 2013/0017246 | A1* | 1/2013 | Tunius | A61F 13/02 424/445 |
| 2013/0041042 | A1 | 2/2013 | Boyden, Jr. | |
| 2013/0089581 | A1 | 4/2013 | Nielsen et al. | |
| 2013/0102947 | A1 | 4/2013 | Auguste | |
| 2013/0123678 | A1 | 5/2013 | Carty et al. | |
| 2013/0133532 | A1 | 5/2013 | Kian et al. | |
| 2013/0138065 | A1 | 5/2013 | Buus | |
| 2013/0138068 | A1 | 5/2013 | Hu et al. | |
| 2013/0158151 | A1 | 6/2013 | Nielsen et al. | |
| 2013/0165838 | A1 | 6/2013 | Auguste et al. | |
| 2013/0226116 | A1 | 8/2013 | Edvardsen et al. | |
| 2013/0226117 | A1 | 8/2013 | Hansen et al. | |
| 2013/0274696 | A1 | 10/2013 | Lam | |
| 2013/0288052 | A1 | 10/2013 | Tapio et al. | |
| 2013/0337260 | A1 | 12/2013 | Tapio et al. | |
| 2014/0031734 | A1 | 1/2014 | Saxena et al. | |
| 2014/0034231 | A1 | 2/2014 | Schubert et al. | |
| 2014/0114265 | A1 | 4/2014 | Israelson et al. | |
| 2014/0114268 | A1 | 4/2014 | Auguste et al. | |
| 2014/0128826 | A1 | 5/2014 | Klein et al. | |
| 2014/0163496 | A1* | 6/2014 | Grum-Schwensen | A61F 5/443 604/338 |
| 2014/0171538 | A1 | 6/2014 | Daniels et al. | |
| 2014/0234584 | A1 | 8/2014 | Hyde et al. | |
| 2014/0348896 | A1 | 11/2014 | Karp et al. | |
| 2014/0358104 | A1 | 12/2014 | Tse et al. | |
| 2015/0018790 | A1 | 1/2015 | Lam et al. | |
| 2015/0030839 | A1 | 1/2015 | Satrijo et al. | |
| 2015/0190983 | A1 | 7/2015 | Caicedo-Carvajal et al. | |
| 2017/0028098 | A1 | 2/2017 | Pearce et al. | |
| 2017/0239384 | A1 | 8/2017 | Lam et al. | |
| 2018/0008451 | A1 | 1/2018 | Stroebech | |
| 2018/0021474 | A1 | 1/2018 | Stroebech et al. | |
| 2019/0117824 | A1 | 4/2019 | Hansen et al. | |

FOREIGN PATENT DOCUMENTS

| | | | | |
|---|---|---|---|---|
| CN | 1073857 | A | 7/1993 | |
| CN | 1199342 | A | 11/1998 | |
| CN | 1258208 | A | 6/2000 | |
| CN | 2430135 | Y | 5/2001 | |
| CN | 102215790 | A | 10/2011 | |
| CN | 102413797 | A | 4/2012 | |
| DE | 102008023798 | A1 | 11/2009 | |
| DE | 102012208597 | A1 | 11/2013 | |
| EP | 0135231 | A1 | 3/1985 | |
| EP | 0300620 | A1 * | 1/1989 | A61L 15/26 |
| EP | 0522250 | A1 | 1/1993 | |
| EP | 2012718 | A1 | 1/2009 | |
| EP | 2305187 | A2 | 4/2011 | |
| EP | 2371920 | A1 | 10/2011 | |
| EP | 2372920 | A2 | 10/2011 | |
| EP | 2654633 | A1 | 10/2013 | |
| FR | 2629833 | A1 | 10/1989 | |
| GB | 1050070 | A | 1/1970 | |
| GB | 2230017 | A | 10/1990 | |
| GB | 2283916 | A | 5/1995 | |
| JP | 07-275282 | A | 10/1995 | |
| JP | 2001-514051 | A | 9/2001 | |
| JP | 2002540817 | A | 12/2002 | |
| JP | 2005-118564 | A | 5/2005 | |
| JP | 2005325101 | A | 11/2005 | |
| JP | 2007-231095 | A | 9/2007 | |
| JP | 2008-073443 | A | 4/2008 | |
| JP | 2010-532183 | A | 10/2010 | |
| JP | 2012-512285 | A | 5/2012 | |
| JP | 2012-530546 | A | 12/2012 | |
| JP | 2013-527860 | A | 7/2013 | |
| RU | 2005113227 | A | 10/2005 | |
| RU | 2341539 | C2 | 12/2008 | |
| WO | 90/13420 | A1 | 11/1990 | |
| WO | 9706836 | A2 | 2/1997 | |
| WO | 98/26811 | A2 | 6/1998 | |
| WO | 9853771 | | 12/1998 | |
| WO | 9855057 | A1 | 12/1998 | |
| WO | 99/18136 | A1 | 4/1999 | |
| WO | 99/29273 | A1 | 6/1999 | |
| WO | 99/36017 | A1 | 7/1999 | |
| WO | 00/14131 | A1 | 3/2000 | |
| WO | 00/61051 | A1 | 10/2000 | |
| WO | 00/61692 | A1 | 10/2000 | |
| WO | 01/85077 | A1 | 11/2001 | |
| WO | 03061720 | A1 | 7/2003 | |
| WO | 2004/108175 | A1 | 12/2004 | |
| WO | 2005/013873 | A1 | 2/2005 | |
| WO | 06038025 | A1 | 4/2006 | |
| WO | 2007/082538 | A1 | 7/2007 | |
| WO | 2007/121744 | A1 | 11/2007 | |
| WO | 2009/000273 | A1 | 12/2008 | |
| WO | 2009/006900 | A1 | 1/2009 | |
| WO | 2009/006901 | A1 | 1/2009 | |
| WO | 2009006902 | A1 | 1/2009 | |
| WO | 2009/087877 | A1 | 7/2009 | |
| WO | 2010/034998 | A1 | 4/2010 | |
| WO | 2010/069333 | A1 | 6/2010 | |
| WO | 2010/148182 | A1 | 12/2010 | |
| WO | 2011/063082 | A2 | 5/2011 | |
| WO | 2011/121303 | A1 | 10/2011 | |
| WO | 2012/048128 | A2 | 4/2012 | |
| WO | 2012/083964 | A1 | 6/2012 | |
| WO | 2012/097199 | A2 | 7/2012 | |
| WO | 2013/022898 | A1 | 2/2013 | |
| WO | 2013/066401 | A1 | 5/2013 | |
| WO | 2013/096530 | A1 | 6/2013 | |
| WO | 2013/148506 | A1 | 10/2013 | |
| WO | 2014/028024 | A1 | 2/2014 | |
| WO | 2014/066195 | A1 | 5/2014 | |
| WO | 2014/080954 | A1 | 5/2014 | |
| WO | 14093246 | A1 | 6/2014 | |
| WO | 2014/202935 | A1 | 12/2014 | |
| WO | 2015132551 | A1 | 9/2015 | |
| WO | 2016055075 | A1 | 4/2016 | |
| WO | 2016124202 | A1 | 8/2016 | |
| WO | 2016124203 | A1 | 8/2016 | |

OTHER PUBLICATIONS

"A permeable pressure sensitive adhesive", Danish patent application PA 2007 01003 filed by Coloplast A/S, Jul. 2007.

Dumitriu, S. "Polymeric Biomaterials, Revised and Expanded", 2001, CRC Press, p. 710.

International Preliminary Report on Patentability received for PCT Patent Application No. PCT/DK2016/050027, dated Jan. 24, 2017, 10 pages.

International Preliminary Report on Patentability received for PCT Patent Application No. PCT/DK2016/050028, dated Jan. 5, 2017, 13 pages.

International Preliminary Report on Patentability received for PCT Patent Application No. PCT/DK2016/050099, dated Jul. 24, 2017, 14 pages.

International Preliminary Report on Patentability received for PCT Patent Application No. PCT/DK2017/050112, dated Mar. 20, 2018, 14 pages.

International Search Report and Written Opinion received for PCT Patent Application No. PCT/DK2016/050027, dated Apr. 20, 2016, 10 pages.

International Search Report and Written Opinion received for PCT Patent Application No. PCT/DK2016/050028, dated Apr. 20, 2016, 11 pages.

International Search Report and Written Opinion received for PCT Patent Application No. PCT/DK2016/050099, dated Jul. 27, 2016, 11 pages.

International Search Report and Written Opinion received for PCT Patent Application No. PCT/DK2017/050112, dated Jun. 9, 2017, 12 pages.

Santini et al., "Photoinitiators in dentistry: a review", Primary Dental Journal, vol. 2, No. 4, p. 30-34, Oct. 2013.

(56) References Cited

OTHER PUBLICATIONS

Neumann et al., "The effect of the mixtures of photoinitiators in polymerization efficiencies", Journal of Applied Polymer Science, vol. 112, p. 129-134, 2008.

Czech et al., "UV-crosslinkable acrylic pressure-sensitive adhesives for industrial application", Polym. Bull., vol. 69, p. 71-80, 2012.

* cited by examiner

OSTOMY DEVICE

Disclosed is an ostomy device with an adhesive wafer for attachment to a skin surface of a user and a collecting bag connected to the adhesive wafer. The adhesive wafer includes a backing layer, a first switchable adhesive composition, a second adhesive composition, and a release liner. The first switchable adhesive is contained in a recess in the device.

BACKGROUND

In connection with surgery for a number of diseases in the gastro-intestinal tract, one of the consequences in many cases is that the patient is left with an abdominal stoma, such as a colostomy, an ileostomy or a urostomy, in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time. Ostomy appliances are typically attached to the skin of the ostomy user by means of an adhesive wafer on the ostomy appliance.

BRIEF DESCRIPTION OF THE DRAWING

The accompanying drawings are included to provide a further understanding of embodiments.

DETAILED DESCRIPTION OF THE INVENTION

Figure 1:
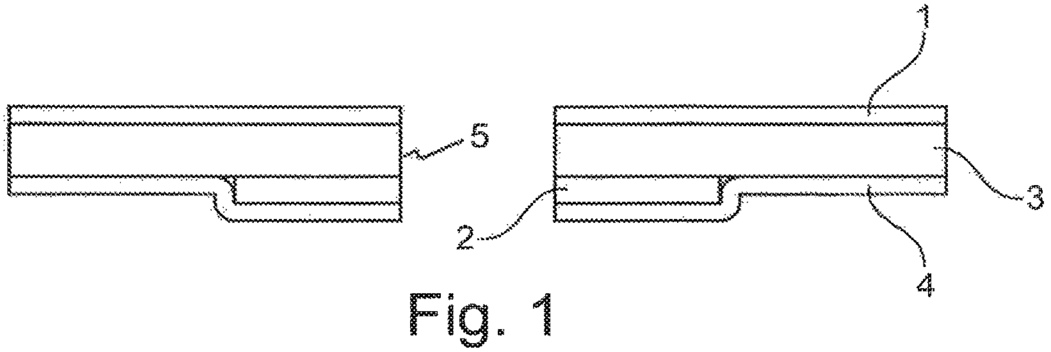
FIG. 1 illustrates an embodiment of an ostomy device in cross-section.

Embodiments provide an ostomy device including an adhesive wafer for attachment to a skin surface of a user, and a collecting bag connected to the adhesive wafer. The collecting bag is suitable for collecting output from the stoma of the user. The adhesive wafer has a through-going hole for accommodating the stoma of the user. In this way, the output from the stoma ends up in the collecting bag. The adhesive wafer includes a backing layer, a first switchable adhesive composition, a second adhesive composition, and a release liner. The first switchable adhesive composition is accommodated in a recess in the device.

In embodiments, the adhesive wafer will have a proximal ("skin-facing") surface, which faces the skin of the user during use, and a distal ("non-skin-facing") surface, which faces away from the user's skin during use. Before use, the proximal surface of the adhesive wafer can be covered by a release liner, which is releasably attached to the adhesive. The release liner can be removed by the user immediately prior to application of the adhesive wafer to the skin. Both before and during use, the distal surface of the adhesive wafer can be made up of a backing layer, which can be used to attach the collecting bag to the adhesive wafer, for instance by welding. As such, the adhesive wafer may comprise a distal backing layer and a proximal release liner, with the first switchable adhesive composition and the second adhesive composition located between the backing layer and the release liner.

Adhesives being soft or even liquid may be excellent with regard to adhesion to the skin, due to their ability to flow into the microstructure and macrostructure of the skin. However, the texture of such adhesives makes it difficult to incorporate them into ostomy devices. The adhesive may flow during storage and application and end up in undesired places.

The first switchable adhesive is contained in a recess in the device. By having the first adhesive in a recess, the adhesive is in a simple manner controlled with regard to flowing as it is contained in the recess and the device can be stored and handled without the adhesive is escaping.

By recess is herein meant a structure that is capable of containing a flowable substance, i.e. a cavity like structure with wall preventing the liquid substance from unintended flowing away from the recess.

In embodiments, the recess is in the release liner. The release liner may be formed, for example thermoformed to comprise a recess for containing at least a part of the first adhesive. The recess will prevent the first adhesive from escaping from the wafer before use.

In embodiments, the recess is in the second adhesive composition. A cavity may be embossed into the second adhesive composition thereby providing a recess for containing the first adhesive. The skin facing surface of the first and the second adhesive composition may be flush in the sense that the skin-facing surface of the wafer is substantially planar.

In embodiments, the recess is partly in the second adhesive composition and partly in the release liner.

In embodiments, the recess is provided by at least a part of the edge portions of the first adhesive have been switched into a form-stable texture. These switched parts of the first adhesive may constitute walls of a recess for containing the adhesive. In embodiments, the switched edge portions have a width of 0.5-3 mm, such as approximately 1 mm. The recess is bound by the walls of switched adhesive and the backing layer or the second adhesive layer.

In an aspect is provided an ostomy device including an adhesive wafer for attachment to a skin surface of a user, and a collecting bag connected to the adhesive wafer. The collecting bag is suitable for collecting output from the stoma of the user. The adhesive wafer has a through-going hole for accommodating the stoma of the user. In this way, the output from the stoma ends up in the collecting bag. The adhesive wafer includes a backing layer, and a first switchable adhesive composition and a release liner. The first switchable adhesive composition is accommodated in a recess in the device.

In embodiments, the recess has a size and shape substantially equal to the size and shape of the layer of the first switchable adhesive.

The release liner may be in contact with both the first switchable adhesive composition and the second adhesive composition.

In embodiments, the first switchable adhesive composition is having in the first liquid state a complex viscosity $|\eta^*|$ below 0.4 MPa s (mega Pascal-second, i.e., MPa·s); and having in the second adhesive state a higher complex viscosity $|\eta^*|$ than the complex viscosity $|\eta^*|$ of the first liquid state, and having in the second adhesive state a second repeated peel force above 1 N.

In embodiments, the first switchable adhesive composition has an inner rim in a radial distance from the through-going hole defining an inward boundary and an outer rim in a radial distance from the through-going hole defining an outward boundary for in a radial distance from the hole. The part of the first adhesive being along the outer rim or edge may be switched in order to provide a more solid and form stable barrier or wall to prevent the first adhesive from flowing. In embodiments, at least the inner or the outer rim of the first switchable adhesive are switched to form a recess for containing the first switchable adhesive.

In embodiments, the layer of the first adhesive may be provided with lines of switched adhesive, providing stability for the first adhesive layer. The lines may divide the first adhesive into compartments, separated by switched walls. The switching of the adhesive along the rim and/or in lines may be done by laser or by a mold. The switched lines may have a width of 0.5-3 mm, such as approximately 1 mm.

In an aspect is provided a method of applying an ostomy device comprising the steps of: providing an ostomy device comprising an adhesive wafer for attachment to a skin surface of a user, and a collecting bag connected to the adhesive wafer; the adhesive wafer having a through-going hole for accommodating the stoma of the user; and the adhesive wafer comprising a backing layer, a first switchable adhesive composition, a second adhesive composition, and at least one release liner, wherein the first switchable adhesive comprises a polymer and a switch initiator, wherein the composition can be switched from a first liquid state to a second adhesive state by activation of the switch initiator, wherein the device comprises a recess for accommodating the first switchable adhesive composition, removing at least a part of the release liner from the device, applying the adhesive wafer to the skin around the stoma, molding the first adhesive to fit around the stoma and switching the first adhesive composition from a first liquid state to a second adhesive state by activation of the switch initiator.

The method may be carried out by a person other than the user to which the adhesive is attached. For instance, the method may be carried out by a commercial service provider assisting the user for a fee. Such commercial service providers exist and provide fee-based services to, e.g., ostomy users or people with wounds. The service may include the service provider removing and applying ostomy bags for the ostomy user or removing and applying wound dressings for a person with wounds.

The method may also be carried out in order to obtain a sample of the output from the ostomy user or wound exudate from the person with wounds. For instance, a healthcare professional may require a stoma output or wound exudate sample in order to make medical decisions or generally assess the physical state of a user. In such cases, the healthcare professional may order the sampling to be done by a professional service provider to ensure that the sampling happens correctly. Again, a fee-based commercial service provider would carry out the method with the aim of providing a sample to the healthcare professional. Such paid services exist on commercial terms and operate on a continuous and independent basis with an aim of financial gain. They are not exclusively dependent for their operation on the instructions of the user in question. For instance, they may work directly under the instructions of a healthcare professional.

In embodiments, the first adhesive may be switched actively by the user for example by exposure to light or moisture or it may switch passively/automatically over time.

In embodiments, an active switch may be fast such as in 10 seconds. A passive switch may be slower, for example be an on-going process from application to removal.

The through-going hole may be cut to fit the stoma prior to application. In embodiments, cutting lines in the form of switched adhesive or lines of reduced thickness may be provided in order to ease the cutting.

In embodiments, the size and shape of the hole may be adapted to fit the stoma by rolling up the edges of the hole.

The texture of the first adhesive allows the user to mold the adhesive into a snug fit around the stoma and it is thus possible to fit the wafer to the stoma without cutting the hole precisely. When the first adhesive is molded to fit the stoma, the adhesive may be switched to achieve a more form stable texture, securing the adhesive stays in place.

The switching of the adhesive may alter the texture from a low cohesion to high cohesion. The low cohesion enables good flow into the structures of the skin and good tack, whereas the high cohesion enables easy removal of the adhesive without leaving residues on the skin.

The first switchable adhesive composition comprising a polymer and a switch initiator, wherein the composition can be switched from a first liquid state to a second adhesive state by activation of the switch initiator.

In embodiments, the first adhesive composition is having in the first liquid state a complex viscosity $|\eta^*|$ below 0.4 MPa s (mega Pascal-second, i.e., MPa·s); and is having in the second adhesive state a higher complex viscosity $|\eta^*|$ than the complex viscosity $|\eta^*|$ of the first liquid state, and is having in the second adhesive state a second repeated peel force above 1 N.

The present inventors have found that the many requirements of an adhesive can be addressed by using a composition that can exists in at least two different states, which have different physical properties and address different requirements of the adhesive. The composition can then at some point be switched from one state to another state, thereby changing its physical properties and the characteristics associated with these properties.

For instance, a composition may have a first state in which it quickly and easily wets the surface to which it is to be adhered and thus achieves a sufficient adhesive attachment. The same composition may have a second state in which it very easily remains securely adhered to the skin and can be properly removed. In such a situation, the composition in its first state could be applied to the skin. Then the composition could be switched to the second state, in which it would remain securely attached.

The first state of the composition can be a first liquid state in which the composition is relatively fluid, i.e. has a low viscosity.

The second state can be a second adhesive state in which the composition possesses good adhesive qualities, for instance by exhibiting the characteristics of a pressure sensitive adhesive. The composition in the second state can be more viscous, i.e. have a higher viscosity, than the composition in the first state.

The composition of the first switchable adhesive can be a skin adhesive composition, i.e. an adhesive composition that is to be used on the skin of a person. The adhesive composition may for instance be used for attaching an ostomy device to an ostomy user.

By combining the properties of the first state and the second state into one composition, an adhesive is obtained that is capable of quickly and effortlessly establishing good adhesion and reliably staying adhered to the skin. The quick and effortless adhesion is achieved by the composition in the first state while the reliable adherence, for instance to skin, is achieved by the composition in the second state.

The switch is the transition from one state to another state of a switchable composition. The duration of the switch will vary depending on, e.g., the nature of the switch initiator and the method of activation of the switch initiator. Generally, the switch will be a gradual process with a gradual change of physical properties of the material from one state to another state. In some instances, the switch will be very fast and the physical properties will change very quickly, e.g. within seconds, to those of the second state. In other instances, the switch will be slower and the change in properties will happen gradually over a period of, e.g., several minutes or even hours. In some embodiments, the activation of the switch initiator comprises exposure of the switch initiator to light or moisture.

In some embodiments, the light comprises visible light and/or UV light. Visible light is defined as electromagnetic radiation with a wavelength in the range 400-700 nm. Ultraviolet light is defined as electromagnetic radiation with a wavelength in the range 10-400 nm.

In some embodiments, the exposure to light has a duration of 10-60 seconds.

For instance, the exposure to light may be less than 60 minutes, less than 30 minutes, less than 10 minutes, less than 5 minutes, less than 4 minutes, less than 3 minutes, less than 2 minutes, less than 1 minute, less than 45 seconds, less than 30 seconds, less than 15 seconds, less than 10 second, less than 5 seconds, 1-10 seconds, 10-30 seconds, 10-60 seconds, 30-60 seconds, 1-2 minutes, 2-3 minutes, 3-4 minutes, or 4-5 minutes.

In some embodiments, the activation of the switch initiator comprises uptake of moisture, e.g. from the surrounding air, into the adhesive composition.

The fast and effective adhesion to the skin effected by the switchable adhesive composition further leads to prevention of leakage of output from the ostomy.

Leakage is when ostomy output makes its way to the skin and clothes outside the ostomy device. This can of course also be damaging to the skin and the adhesive and is, obviously, also problematic to the user in terms of discomfort and smell. Leakage typically results from ostomy output having first leaked into the adhesive and then through the adhesive to the outside, or into the space between the skin and the adhesive and then to the outside. As such, preventing leakage between the adhesive and the skin as well as into the adhesive will also prevent most types of leakage outside of the ostomy device. A special kind of leakage is when the ostomy bag partly or entirely detaches from the skin of the user during use, thus causing the output in the collecting bag to directly spill out. This type of leakage is best prevented by ensuring a strong a durable adhesive bond between the skin of the user and the ostomy device. Also, detachment will typically be a result of the adhesive having been weakened during the course of use, for instance by being affected by the output. As such, ensuring a strong and enduring adhesive bond and preventing leakage will also minimize the risk of the adhesive detaching from the skin and the bag falling off.

By using a switchable adhesive composition with a pre-switch low viscosity, a quick initial adherence between the adhesive and the skin of the user can take place as well as it is possible to mold the adhesive into a snug fit around the stoma. The low viscosity of the adhesive allows it to blend into the structure, wrinkles and folds of the skin to facilitate a tight-fitting adhesion to the skin. This will, already from application of the adhesive to the skin, prevent output from leaking into the space between the skin and the adhesive. This is in contrast to some non-switchable pressure sensitive adhesives, which typically require a significant amount of time, such as 10-60 minutes, to achieve strong adhesion. By applying pressure to the pressure sensitive adhesive it is possible for the adhesive to wet and flow faster into the skin surface, hereby obtaining a large contact area and hereby increasing the adhesive power. Some current adhesive systems for attachment of ostomy devices to the skin require a high or prolonged pressure from the user in order to sufficiently flow into and wet the surface of the substrate. By using a switchable adhesive with an initial low viscosity, neither a high pressure nor a long time is needed in order to ensure a good and enduring adhesion to the skin.

The quick and effective initial bonding of the switchable adhesive is thought to be at least partly the result of the ability of the switchable adhesive to quickly wet the skin, meaning that it will quickly flow into both the macro- and micro-structures of the skin and thereby establish a large contact surface between the adhesive and the skin. This flowing of the adhesive into the skin is a common phenomenon for pressure sensitive adhesives, but the speed at which it happens, and hence how quickly a strong adhesive bond is formed, varies widely for different compositions.

Typically, ostomy users will want to be able to move around shortly after having applied the ostomy device to the skin. Such movements can increase the risk of leakage if the adhesive has not yet achieved strong adhesion to the skin. With a switchable adhesive composition the risk of such leakage soon after application is reduced because of the rapidly forming effective adhesive bond. Switching the first adhesive after application to the skin may provide the adhesive with a higher viscosity and form stability as well as detachment of the wafer may be easier, due to a higher cohesion of the adhesive.

In embodiments, the first switchable adhesive composition is in contact with the backing layer. The first switchable adhesive composition may be disposed on the backing layer or coated on the backing layer. By being in contact with the backing layer, at least part of the switchable adhesive composition is close to the distal non-skin-facing surface of the adhesive wafer. This will make it easier to effect the switch of the switchable adhesive composition, for instance by applying light to the switchable adhesive composition through the backing layer. In embodiments, the first switchable adhesive may fully cover the backing layer or it may be disposed on a part of the backing layer. If a second adhesive is present it may cover the remaining part of the backing layer.

In embodiments, the release liner is in contact with both the first switchable adhesive composition and the second adhesive composition. The release liner covers the surface of the adhesive that is to be attached to the skin of the user. As such, the surface of the adhesive that is in contact with the release liner is also the surface that will be in contact with the skin of the user during use. By having both the first switchable adhesive composition and the second adhesive composition form part of the adhesive surface that comes into contact with the user's skin, it is ensured that both adhesives can exert their respective effects directly on the skin. In other words, both adhesive compositions will be in contact with the user's skin during use.

In embodiments, the adhesive wafer has a central part adjacent to the through-going hole for accommodating the stoma and a peripheral part adjacent to an edge of the adhesive wafer away from the hole. The first switchable adhesive composition may be located at least in the central part of the adhesive wafer. The central part of the wafer is the part that is closer to the through-going hole in the wafer than it is to the peripheral edge of the wafer. Typically, this will represent a ring-shaped area of the adhesive wafer surrounding the hole. The central part will be the part of the wafer that is closest to the stoma during use of the ostomy device. The peripheral part is the remainder of the adhesive wafer outside the central part, i.e., the part that is closer to the peripheral edge than to the hole. Typically, the peripheral part will also be a ring-shaped area of the adhesive wafer. The adhesive may be in the entire peripheral part of the wafer. The second adhesive may extend also to the central part of the adhesive wafer.

In embodiments, the first switchable adhesive composition is located only in the central part of the adhesive wafer. The first switchable adhesive composition may be located as a ring-shaped element in the central part of the adhesive wafer, thus surrounding the stoma during use.

In embodiments, the second adhesive composition is located at least in the peripheral part of the adhesive wafer. The second adhesive composition may be in the entirety of the peripheral part or only in part of the peripheral part of the wafer. The second adhesive composition may extend into the central part of the wafer.

In embodiments, the releaser liner is in contact with the first adhesive composition in the central part of the adhesive wafer. In this manner, the first adhesive will be in contact with the skin surrounding the stoma during use. This will allow the first adhesive to be molded to seal around the stoma. In embodiments, the backing layer is suitably elastic, i.e. it has a low modulus, enabling the adhesive construction to conform to the skin movement and provide comfort when using it. The backing layer may have a structured surface to improve the adhesion between the adhesive and the backing layer. The backing layer may be a non-woven or a non-woven-film laminate. The backing layer may be a polymer film. The backing layer may comprise polyurethane. The thickness of the backing layer is dependent on the type of backing layer used. For polymer films, such as polyurethane films, the overall thickness may be between 10 to 100 micrometers, such as between 20 to 50 micrometers, such as about 20-30 micrometers.

The release liner may be of any material known to be useful as a release liner for medical devices. For instance, the release liner may be in the form of a polymer film, foil, or paper, having release properties that enable the adhesive to be released easily from the liner. Such properties may be inherent in the material or the layer may be siliconized, coated with a low surface tension coating, or subjected to other appropriate surface modifications. Release liners are in general made on a mechanically stiff backing such as paper, polyethylene, polypropylene, or polyethylene terephthalate. This stiffness will support the adhesive wafer when applying the collecting device. The release lines may be thermo-formed into a form stable shape, such as having a recess for accommodating at least a part of the first adhesive composition.

In embodiments, the first switchable adhesive composition is in the form of a ring-shaped adhesive element located around the hole in the adhesive wafer and in contact with the release liner. Such a ring-shaped adhesive element could have a diameter of 30-70 mm, such as 40-70 mm, such as 50-70 mm, such as 60-70 mm. The ring-shaped adhesive element could for instance have a diameter of 30 mm, 40 mm, 50 mm, 60 mm, or 70 mm. The ring-shaped element could have a width, i.e. the distance from the inner rim of the ring to the outer rim of the ring measured along the surface of the ring, of at least 10 mm, at least 20 mm, at least 30 mm, at least 40 mm, at least 50 mm, 10-20 mm, 10-30 mm, 10-50 mm, 20-30 mm, 20-40 mm, 20-50 mm, 30-40 mm, 30-50 mm, or 40-50 mm. The width of the element can be constant over the entire element or it may vary.

In embodiments, the second adhesive composition extends in the entire area of the adhesive wafer. In embodiments, the second adhesive composition is in the form of a ring-shaped adhesive element located at the periphery of the adhesive wafer. Such a ring-shaped second adhesive element could have a diameter of 50-150 mm, such as 50-120 mm, such as 50-100 mm, such as 50-75 mm. The ring-shaped adhesive element could for instance have a diameter of 50 mm, 60 mm, 70 mm, 80 mm, 90 mm, 100 mm, 120 mm, or 150 mm. The ring-shaped element could have a width of at least 10 mm, at least 20 mm, at least 30 mm, at least 40 mm, at least 50 mm, at least 60 mm, at least 70 mm, at least 80 mm, at least 90 mm, at least 100 mm, 10-20 mm, 10-30 mm, 10-50 mm, 10-100 mm, 20-30 mm, 20-40 mm, 20-50 mm, 20-100 mm, 30-40 mm, 30-50 mm, 30-100 mm, 40-50 mm, 40-100 mm, or 50-100 mm. The width of the element can be constant over the entire element or it may vary.

An adhesive element could also have an only roughly ring-shaped, oval, or roughly oval form. In that case, the mentioned diameters would be the maximum distance from one point on the outer edge of the element to another point on the outer edge of the element. The adhesive element may be asymmetric in shape.

In embodiments, the first switchable adhesive composition has a uniform thickness, i.e. the distance from one outer surface of the adhesive to the other outer surface of the adhesive measured in a straight line perpendicular to the surface of the adhesive. In embodiments, the uniform thickness of the first adhesive composition is at least 50 micrometers, such as at least 100 micrometers, such as at least 200 micrometers, such as at least 300 micrometers, such as at least 400 micrometers, such as at least 500 micrometers, such as at least 750 micrometers, such as at least 1,000 micrometers, such as at least 1,500 micrometers, such as at least 2,000 micrometers, such as at least 3,000 micrometers such as at least 4,000 micrometers. The uniform thickness of the first adhesive composition may be between 50 micrometers and 1,000 micrometers, such as 100-500 micrometers, such as 200-400 micrometers, such as 200-300 micrometers. The uniform thickness of the first adhesive composition may be 50-250 micrometers, 100-250 micrometers, 250-500 micrometers, 250-750 micrometers, 500-750 micrometers, 500-1,000 micrometers, 500-1,500 micrometers, 500-2,000 micrometers, 1,000-1,500 micrometers, 1,000-1,500 micrometers, 1,000-2,000 micrometers, or 1,500-2,000 micrometers.

In embodiments, the first switchable adhesive composition has a varied thickness. In embodiments, the second adhesive composition has maximum thickness of at least 50 micrometers, such as at least 100 micrometers, such as at least 200 micrometers, such as at least 300 micrometers, such as at least 400 micrometers, such as at least 500 micrometers, such as at least 750 micrometers, such as at least 1,000 micrometers, such as at least 1,500 micrometers, such as at least 2,000 micrometers. The maximum thickness of the first adhesive composition may be between 50 micrometers and 1,000 micrometers, such as 100-500 micrometers, such as 200-400 micrometers, such as 200-300 micrometers. The maximum thickness of the first adhesive composition may be 50-250 micrometers, 100-250 micrometers, 250-500 micrometers, 250-750 micrometers, 500-750 micrometers, 500-1,000 micrometers, 500-1,500 micrometers, 500-2,000 micrometers, 1,000-1,500 micrometers, 1,000-1,500 micrometers, 1,000-2,000 micrometers, or 1,500-2,000 micrometers, or 1,500-3000, or 1,500-4,000 micrometers.

In embodiments, the second adhesive composition has a uniform thickness. In embodiments, the uniform thickness of the first adhesive composition is at least 10 micrometers, such as at least 25 micrometers, such as at least 50 micrometers, such as at least 100 micrometers, such as at least 200 micrometers, such as at least 300 micrometers, such as at least 400 micrometers, such as at least 500 micrometers, such as at least 750 micrometers, such as at least 1,000 micrometers. The uniform thickness of the first adhesive composition may be between 10 micrometers and 1,000 micrometers, such as 25-500 micrometers, such as 50-500 micrometers, such as 100-500 micrometers, such as 200-400 micrometers, such as 200-300 micrometers. The uniform thickness of the first adhesive composition may be 10-50 micrometers, 10-100 micrometers, 25-50 micrometers, 25-100 micrometers, 50-100 micrometers, 50-250 micrometers, 100-250 micrometers, 250-500 micrometers, 250-750 micrometers, 500-750 micrometers, 500-1,000 micrometers.

In embodiments, the second adhesive composition has a varied thickness. In embodiments, the maximum thickness of the second adhesive composition is at least 10 micrometers, such as at least 25 micrometers, such as at least 50 micrometers, such as at least 100 micrometers, such as at least 200 micrometers, such as at least 300 micrometers, such as at least 400 micrometers, such as at least 500 micrometers, such as at least 750 micrometers, such as at least 1,000 micrometers. The maximum thickness of the second adhesive composition may be between 10 micrometers and 1,000 micrometers, such as 25-500 micrometers, such as 50-500 micrometers, such as 100-500 micrometers, such as 200-400 micrometers, such as 200-300 micrometers. The maximum thickness of the second adhesive composition may be 10-50 micrometers, 10-100 micrometers, 25-50 micrometers, 25-100 micrometers, 50-100 micrometers, 50-250 micrometers, 100-250 micrometers, 250-500 micrometers, 250-750 micrometers, 500-750 micrometers, 500-1,000 micrometers. In embodiments, the second adhesive composition is thicker in the peripheral part of the adhesive wafer than in the central part of the adhesive wafer. In embodiments, a thickness of the second adhesive composition in the peripheral part of the adhesive wafer is at least 120%, such as at least 150%, such as at least 200%, such as at least 250%, such as at least 500% of a thickness of the second adhesive composition in the central part of the adhesive wafer.

In embodiments, the second adhesive composition is disposed on the backing layer and covers the entire backing layer. The first adhesive composition is in the form of a ring-shaped adhesive element in the center of the adhesive wafer around the hole and on the skin-facing surface of the second adhesive composition. In this manner, the second adhesive composition will be in contact with the release liner in the periphery of the wafer and the first adhesive composition will be in contact with the release liner in the center of the wafer. Both adhesives will therefore be in contact with the skin of the user during use.

Polymer component: Acrylates

In embodiments, the composition comprises an acrylate, including methacrylates and their copolymers. Acrylate copolymers are especially preferred, e.g., alkyl acrylate copolymers.

The most commonly used monomers in polyacrylates include ethyl acrylate, butyl acrylate, ethylhexyl acrylate, hydroxyethyl acrylate, lauryl acrylate, and acrylic acid. They may be used singly or in a mixture, their relative proportions in the mixture being selected depending on the desired viscoelastic properties, glass transition temperature, compatibility etc.

The polymer may be a copolymer with one or more acrylates. Alternatively, the polymer may be a copolymer with one or more acrylates and a free radical polymerisable vinyl moiety. Such vinyl moieties include compounds such as itaconic anhydride, maleic anhydride or vinyl azlactone or glycidyl methacrylate.

The polymer may be a homopolymer, a random copolymer or a block copolymer. The polymer may be branched or linear.

The composition may include bound-in curable moieties. Any conventionally known unsaturated compounds, e.g. olefinic or aromatic compounds may be used or compounds with labile groups or groups which can undergo free radical reactions, could be used as the curable molecules. Photoreactive groups may also be used and include groups such as anthracenes, cinnamates, maleimides and coumarin groups. Other functional groups include carboxyl, epoxy, urethane, siloxane, amides, and hydroxyl. Mixtures of all of the above may also be used. The bound-in curable groups may be end groups, pendant groups or may be incorporated into the backbone.

The polymer backbone may be partially cross-linked. Crosslinking can be achieved by incorporating monomers of e.g. N-methylol acrylamide, N-(iso-butoxymethylene)-acrylamide, methyl acrylamidoglycolate methyl ether (all 0.5-5% (w/w)) or metal chelates, e.g., acetylacetonates of Zr, Al, or Fe (up to 2% (w/w) of polymer weight), into the polymer backbone, which then crosslinks during drying after spreading on a substrate. Al and Ti acetylacetonates and similar compounds can also be added after polymerization in concentrations of 0.1-2% (w/w) and used as an crosslinker through utilizing carboxylic groups in the polymer backbone during the drying step.

Multi functional isocyanates, like toluene diisocyante (TDI), trimethyl hexamethylene diisocyanate (TMDI), and hexamethylene diisocyante (HDI), can be used to chemically link hydroxylic or carboxylic functions of different polymer chains, added in concentration up to 1% (w/w).

Crosslinking can also be achieved between the carboxylic groups in the polymer backbone and added amino resins, such as derivatives of melamine, benzoguanamine, glycoluril, and urea, e.g., hexamethoxymethyl melamine, methoxymethyl methylol melamine, methoxymethyl ethoxymethyl benzoguanamine, tetrabutoxymethyl glycoluril, butoxymethyl methylol urea, in concentrations up to 6% (w/w).

The above mentioned cross-linking can also be achieved using polycarbodiimides or multifunctional propylene imines.

It is also possible to blend one or more polymers having high cohesive strength with one or more polymers having low cohesive strength in order to achieve the desired balance.

The polymer will most often be soluble in, and hence commercially supplied as solutions in, organic solvents such as ethyl acetate, hexane, toluene, acetone, etc. Preferably, the polymer is non-water-soluble.

The polymer may be a commercially available PSA or PSA precursor, e.g. acResin A 204 UV, acResin A 260 UV (BASF), Aroset 1450-Z-40, Aroset S390 (Ashland), GMS 788, GMS 1753 (Henkel).

The polymer may include curable molecules which may be low molecular weight monomers or oligomers. In the broadest sense, any conventional known unsaturated compounds, or compounds with labile groups or groups which can undergo free radical reactions, could be used as the curable molecules. Preferred examples, used alone or in mixtures, are curable molecules such as acrylic acid esters or methacrylic acid esters of alcohols, glycols, pentaerythritol, trimethylpropane, glycerol, aliphatic epoxides, aromatic epoxides including bisphenol A epoxides, aliphatic urethanes, silicones, polyesters and polyethers, as well as ethoxylated or propoxylated species thereof.

The curable molecules can have more than one unsaturated or reactive site. With more than a single functionality they enable chain extension. With multiple functionalities of three or greater they are able to form crosslinked three-dimensional polymeric networks. Examples include CN925 (Arkema), Ebecryl 870 (Allnex).

Preferably, the curable molecules and the polymer are soluble in each other when in the dry state, i.e., in the absence of a solvent. Alternatively, in the case that the polymer and the curable molecules are not mutually soluble in each other when dry, or are only partly mutually soluble, they are uniformly dispersed in the composition.

In embodiments, the composition comprises a silicone polymer.

Moisture curing materials are polymeric materials that change from a liquid to a solid state when exposed to moisture. When these materials solidify, they are capable of sustaining deforming forces.

Moisture curing materials may comprise several components including a reactive polymer, a catalyst, a viscosity modifier, a crosslinker, and a water scavenger. The function of the reactive polymer together with a catalyst and a crosslinker is to form a polymer network upon exposure to moisture. This event makes moisture curing materials change from a liquid to a solid state. This may be referred to as "switching" or "curing".

The function of a viscosity modifier is to tune the viscosity to fulfil the requirements of each application. The function of the water scavenger is to prevent unintended curing in the container.

Moisture curing materials may be in one part or in two parts. In case of one-part moisture curing materials, all components may be mixed and stored in a single container until use. Curing starts only once the moisture curing material is open and exposed to moisture. On the other hand, in case of two-component systems, reactive components are isolated from each other in different containers during storage, and come into contact only at the time of use. The reactive components are mixed shortly before use. Curing starts as soon as the reactive components are mixed.

The change of properties from liquid to an adhesive state in moisture curing materials is usually based on condensation cure chemistry.

There is a variety of base polymers with different backbone chemistries, which can lead to condensation cure. Silicone polymers may be used in condensation cure compositions. In order to react via condensation cure, silicones may be terminated with hydroxyl groups in both ends. In the presence of a multifunctional silane, which acts both as cross-linker and water scavenger, catalyst and moisture, hydroxyl terminated silicones will cure. The reactivity of silanol groups vary with the number of electron-withdrawing groups substituents on the silicon atom.

The substituents on the multifunctional cross-linker is a relevant parameter, which may affect the cure speed. A trifunctional, tetrafunctional, and even higher functional oligomeric and polymeric cross-linkers can be employed. In embodiments, different substituents, such as methyl, ethyl, and vinyl groups may be used. Examples of trifunctional cross-linkers based on alkoxy groups include methyl trimethoxy silane and methyl triethoxy silane. In addition to alkoxy, acetoxy, oxime, amine, amide, and enoxy cure systems are available.

The curing systems may be adapted to different applications depending on by-products of the curing process. For example, for ostomy care, by-products should be non-toxic and should not have a bad smell.

A suitable condensation cure catalyst is chosen depending on the chemistry of the multifunctional silane. Titanates are employed with alkoxy, amide, or mime systems, whereas tin catalysts may be added to acetoxy, oxime, and amine cure formulations. In embodiments, the titanate catalyst used is selected from tetraalkoxy titanates and chelated titanates. Tetraalkoxy titanates are the more catalytically active species.

The rate of condensation curing depends on the cross-linking agent (its functionality, concentration and chemical structure), the type of catalyst, and the relative humidity of the environment.

Moisture curing formulations are interesting materials for applications in ostomy care, either as an accessory or as a full device. Some relevant features to consider for moisture curing compositions to be used in ostomy care:

- Safe to use on skin: Moisture curing formulations should be non-toxic before and after cure since they will meet skin.
- Adhesion to skin: Moisture curing formulations should adhere to skin before and after cure. Otherwise, these materials will provide a weak interface between the skin and ostomy care device.
- Handle moisture from body: Ostomy care products should handle moisture, which comes from skin, output, and sweat. Otherwise, water remaining on the skin weakens the adhesion.
- Stable during storage: Moisture curing formulations should be stable during storage in the factory and transportation, but also in the hands of the users before use. Depending on the geographic location, the temperature, and relative humidity of the environment changes. Moisture curing formulations should be stable enough not to cure when exposed to temperatures relevant to storage, transportation, and use situation. In addition, they should be packaged in a way that the moisture cannot diffuse into their container.

Commercially available moisture curing formulations used, e.g., in the construction industry are typically not safe for use on skin. The commercially available "Trio Silken Stoma Gel" from Trio Healthcare is approved for use on skin. However, Trio Silken Stoma Gel has major shortcomings, since it does not adhere to skin and does not absorb body fluids.

Typically, moisture-curing materials for ostomy care applications include a reactive component to cure, a water absorbing component to absorb moisture from the body, and an adhesive component to enable skin adhesion. A straightforward strategy to obtain skin adhesives based on moisture curing is to mix unreactive polymers with adhesive character with reactive components, which on their own do not adhere to skin before and after cure. Such materials will be adherent to skin before and after cure. Employing such a strategy opens the opportunity of using a variety of reactive materials available in other industries after necessary modifications to fulfil the bio-safety requirements for skin application. As the water-absorbing component, e.g., natural hydrocolloids or synthetic hydrophilic polymers can be used.

Adding a water-absorbing component to moisture curing formulations may lead to additional considerations, since some water may be present in natural hydrocolloids or synthetic hydrophilic polymers, which may cause undesired effects with regard to both curing speed and storage stability. A way to minimize such effects is careful drying of water absorbing components prior to their addition to moisture curing formulations.

A switch initiator is a component of a switchable composition, which component upon activation is able to trigger a switch of the switchable composition.

In embodiments the switch initiator comprises or consists of a free radical generating switch initiator. The free radical generating switch initiator may be a photoinitiator. Different photoinitiator systems exist. Photoinitiator systems can be (a) low molecular weight single component, (b) low molecular weight multiple component, (c) polymeric single component, or (d) polymeric multi-component. These systems can be built using chemicals named below and/or polymers containing these functionalities.

In the present invention, a photoinitiator is defined as a moiety which, on absorption of light, generates reactive species (ions or radicals) and initiates one or several chemical reactions or transformation. In some embodiments a preferred property of the photoinitiator is good overlap between the UV light source spectrum and the photoinitiator absorption spectrum. In some embodiments, a desired property is a minor or no overlap between the photoinitiator absorption spectrum and the intrinsic combined absorption spectrum of the other components in the composition.

Suitably, the photoinitiator moieties are pendant on the polymer. This means that they are attached to the polymer at points other than at the polymer ends, thus making it possible to attach more than two photoinitiator moieties to a single polymer.

The photoinitiator moieties of the invention may independently be cleavable (Norrish Type I) or non-cleavable (Norrish Type II). Upon excitation, cleavable photoinitiator moieties spontaneously break down into two radicals, at least one of which is reactive enough to abstract a hydrogen atom. Benzoin ethers (including benzil dialkyl ketals), phenyl hydroxyalkyl ketones and phenyl aminoalkyl ketones are examples of cleavable photoinitiator moieties.

In embodiments, the photoinitiator is efficient in transforming light from the UV or visible light source to reactive radicals which can abstract hydrogen atoms and other labile atoms from polymers, and hence effect covalent cross-linking. Optionally, amines, thiols and other electron donors can be either covalently linked to a polymeric photoinitiator or added separately or both. The addition of electron donors is not required but may enhance the overall efficiency of cleavable photoinitiators according to a mechanism similar to that described for the non-cleavable photoinitiators below.

In embodiments the photoinitiator of the invention is non-cleavable (Norrish Type II). Non-cleavable photoinitiators do not break down upon excitation, thus providing fewer possibilities for the leaching of small molecules from the composition. Excited non-cleavable photoinitiators do not break down to radicals upon excitation, but abstract a hydrogen atom from an organic molecule or, more efficiently, abstract an electron from an electron donor (such as an amine or a thiol). The electron transfer produces a radical anion on the photoinitiator and a radical cation on the electron donor. This is followed by proton transfer from the radical cation to the radical anion to produce two uncharged radicals; of these the radical on the electron donor is sufficiently reactive to abstract a hydrogen atom.

Benzophenones and related ketones such as thioxanthones, xanthones, anthraquinones, fluorenones, dibenzosuberones, benzils, and phenyl ketocoumarins are examples of non-cleavable photoinitiators. Most amines with a C—H bond in α-position to the nitrogen atom and many thiols will work as electron donors. An advantage of using Norrish Type II as opposed to Type I photoinitiators is fewer generated by-products during photoinitiated reactions. As such benzophenones are widely used. When for example α-hydroxy-alkyl-phenones dissociate in a photoinitiated reaction, two radicals are formed, which can further dissociate and possibly form loosely bound unwanted aromatic by-products.

Self-initiating photoinitiator moieties may also be used. Upon UV or visible light excitation, such photoinitiators predominantly cleave by a Norrish type I mechanism and cross-link further without any conventional photoinitiator present, allowing thick layers to be switched. Recently, a new class of β-keto ester based photoinitiators has been introduced.

In some embodiments, the switch initiator comprises at least two different types of photoinitiators. The absorbance peaks of the different photoinitiators are at different wavelengths, so the total amount of light absorbed by the system increases. The different photoinitiators may be all cleavable, all non-cleavable, or a mixture of cleavable and non-cleavable. A blend of several photoinitiator moieties may exhibit synergistic properties. In some embodiments the switch initiator comprises a mix of different photoinitiators, such as two, three, four, or five different photoinitiators.

Examples of photoinitiators absorbing in the 200-400 nm range include α-hydroxyketone, benzophenone, benzophenone derivatives, benzophenone/α-hydroxyketone, phenylglyoxylate, benzyldimethyl-ketal, aminoketone, acylphosphine oxide derivatives, mono acyl phosphine (MAPO), MAPO/α-Hydroxyketone, bis acyl phosphine (BAPO), BAPO dispersion, BAPO/α-hydroxyketone, phosphine oxide, metallocene, ionium salt, thioxanthone derivatives, mixture of triarylsulphonium hexafluorophosphate salts in propylene carbonate, mixture of triarylsulphonium hexafluoroantimonate salts in propylene carbonate, camphorquinone derivatives, benzil derivatives, anthraquinone derivatives, benzoin ether derivatives, and polysilanes.

Specific examples of photoinitiators include 2-Benzyl-2-(dimethylamino)-4'-morpholinobutyrophenone, 2-Methyl-4'-(methylthio)-2-morpholinopropiophenone, (Benzene) tricarbonylchronium, (Cumene)cyclopentadienyliron(II) hexafluorophophate, dibenzosuberenone, ferrocene, and methylbenzoylformate.

Other examples include aromatic ketones useful in the 200-400 nm range, e.g. acetophenone; camphorquinone+iodonium salt+silane (which may be useful in obtaining efficient photoinitiation in air); peroxides, e.g. benzoyl peroxide; and azo compounds, e.g. 2,20-azobisisobutyronitrile.

In the >400 nm range examples of photoinitiators include carbazole derivatives, metallocene, thioxanthone derivatives, camphorquinone derivatives, benzil derivatives, titanocenes, anthraquinone derivatives, acylphosphine derivatives, keto-coumarins, xanthenic dyes (e.g. erythhrosin B), thioxanthone derivatives (e.g. 2-chlorothioxanthone, 2-isopropylthioxanthone, 2-mercaptothioxanthone, thioxanthone acetic acid derivatives) optionally in combination with amines, and benzophenones optionally in combination with amines.

In embodiments the switch initiator comprises or consist of bis(.eta.5-2,4-cylcopentadien-1-yl)-bis(2,6-difluoro-3-(1H-pyrrol-1-yl)-phenyl) titanium (Ciba Irgacure 784).

In embodiments, the second adhesive composition comprises a polymer comprising monomer units selected from the group consisting of styrene, isoprene, butadiene, ethylene, and butylene.

In embodiments, the second adhesive composition comprises a styrene block co-polymer.

In embodiments, the second adhesive composition comprises a styrene block co-polymer selected from the group consisting of styrene-isoprene-styrene (SIS), styrene-butadiene-styrene (SBS), styrene-isobutylene-styrene (SIBS), and styrene-ethylene/butylene-styrene (SEBS).

In embodiments, the second adhesive composition comprises a polyethylene copolymer.

In embodiments, the second adhesive composition comprises a polyethylene copolymer selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

In embodiments, the second adhesive composition comprises polyisobutylene (PIB).

In embodiments, the second adhesive composition comprises absorbent material. In embodiments, the second adhesive composition comprises water absorbent material.

In embodiments, the second adhesive composition comprises absorbent material selected from the group consisting of hydrocolloids, microcolloids, salt, and super absorbent particles.

In embodiments, the second adhesive composition comprises an absorbent material in an amount of 1-60% (w/w) of the composition.

For instance, the second adhesive composition comprises an absorbent material in an amount of 1-40% (w/w) or 1-20% (w/w) or 20-40% (w/w) or 20-60% (w/w) or 40-60% (w/w) or 25-50% (w/w) of the composition.

In embodiments, the absorbent material is selected from hydrocolloid, water soluble salt, mono, di- and oligosaccharides, sugar alcohols, polypeptides, organic acids, inorganic acids, amino acids, amines, urea, super absorbent particles such as polyacrylic acid, glycols such as polyethylene glycol, fumed silica, bentone, and mixtures thereof.

In embodiments, the hydrocolloid is selected from guar gum, locust bean gum, pectin, potato starch, alginates, gelatine, xantan or gum karaya, cellulose derivatives, salts of carboxymethyl cellulose, sodium carboxymethyl cellulose, methyl cellulose, hydroxypropyl cellulose, hydroxyethyl cellulose, sodium starch glycolate, polyvinylalcohol, and mixtures thereof.

In embodiments, the water soluble salt is selected from NaCl, $CaCl_2$, $K_2SO_4$, $NaHCO_3$, $Na_2CO_3$, KCl, NaBr, NaI, KI, $NH_4Cl$, $AlCl_3$, $CH_3COONa$, $CH_3COOK$, HCOONa, HCOOK, and mixtures thereof.

In embodiments, the adhesive composition may comprise ingredients such as tackifiers, extenders, non-reactive polymers, oils (e.g. polypropyleneoxide, ethyleneoxide-propyleneoxide copolymers, mineral oil), plasticizers, fillers, and surfactants.

One element in forming the adhesive bond is the flow of the adhesive composition into the micro- and macro-structure of the substrate. The better the adhesive composition is able to flow into, i.e. wet, the substrate, the larger the adhesive contact area obtained. A large contact area between the adhesive and the substrate will lead to improved adhesion. Wetting of a substrate by an adhesive composition is dependent on the characteristics of the composition as well as upon, e.g., time, temperature, and pressure. In relation to wetting of a substrate, a central characteristic of an adhesive composition is the viscosity, measured herein as the complex viscosity $|\eta^*|$.

In embodiments, the switchable adhesive composition has a complex viscosity $|\eta^*|$ below 400,000 Pa s, 300,000 Pa s, 200,000 Pa s, below 150,000 Pa s, below 100,000 Pa s, below 75,000 Pa s, below 50,000 Pa s, below 25,000 Pa s, below 10,000 Pa s, below 5,000 Pa s, below 1,000 Pa s, below 500 Pa s, below 250 Pa s, below 100 Pa s, below 50 Pa s, or below 10 Pa s measured as described herein. In embodiments, the switchable adhesive composition has a complex viscosity $|\eta^*|$ of 10-50 Pa s, 50-100 Pa s, 100-250 Pa s, 250-500, Pa s, 500-1,000 Pa s, 1,000-5,000 Pa s, 5,000-10,000 Pa s, 10,000-25,000 Pa s, 25,000-50,000 Pa s, 50,000-75,000 Pa s, 75,000-100,000 Pa s, 100,000-150,000 Pa s, 150,000-200,000 Pa s, 200,000-300,000 Pa s, 300,000-400,000 Pa s, 400,000-500,000 Pa s, 10-100 Pa s, 100-1,000 Pa s, 1,000-10,000 Pa s, 10,000-100,000 Pa s, or 100,000-500,000 Pa s.

Complex viscosity is a measure of the resistance to gradual deformation of a given liquid state composition. Generally, the lower the viscosity, the more quickly the composition will be able to wet a rough surface by flowing into the small structures of the surface, such as the microstructure of skin.

In the present context, a relatively low complex viscosity is advantageous in that it will lead to the composition more easily and quickly flowing into the contour of the skin.

An advantage of this low viscosity is that the adhesive in the first state will be able to easily and quickly flow into, i.e. wet, the microstructure of the skin as well as larger irregularities, such as scar tissue and wrinkles. This means that a large contact surface between the adhesive and the skin is quickly established and that a good adhesive bond between the skin and the adhesive is quickly obtained.

In embodiments, the complex viscosity of the switchable adhesive composition after switch is at least 2 times, such as at least 5 times, such as at least 10 times, such as at least 20 times, such as at least 50 times, such as at least 100 times, such as at least 1,000 times, such as at least 10,000 times higher than the complex viscosity of the switchable adhesive composition before switch.

Measurement Methods

Dynamic Mechanical Analysis (DMA) and Determination of Complex Viscosity $|\eta^*|$ The parameter complex viscosity 10 was measured as follows by a frequency sweep. The adhesives were pressed into a plate of 1 mm thickness. A round sample of 25 mm in diameter was cut out and placed in a Haake RheoStress 6000 rotational rheometer from Thermo Scientific. The geometry applied was parallel plates 25 mm and the shear stress was fixed at 5556 Pa and a gap size of 0.9-1.05 mm was applied to the sample in the beginning of the measurement to obtain a normal force of approximately 5 N. The measurements were carried out at 32° C. For the complex viscosity $|\eta^*|$ the value measured at a frequency of 0.01 Hz was used.

Moisture Vapour Transmission Rate

Moisture vapour transmission rate (MVTR) is measured in grams per square meter ($g/m^2$) over a 24 hours period using an inverted cup method.

A container or cup that was water and water vapour impermeable having an opening of Ø35 mm was used. 20 mL saline water (0.9% NaCl in demineralised water) was placed in the container and the opening was sealed with the test adhesive mounted on a highly permeable polyurethane (PU) backing film (BL9601 foil from Intellicoat). The container was placed into an electrically heated humidity cabinet and the container or cup was placed upside down, such that the water was in contact with the adhesive. The cabinet was maintained at 32° C. and 15% relative humidity (RH).

The weight loss of the container was followed as a function of time. The weight loss was due to water transmitted through the adhesive and/or film. This difference was used to calculate the MVTR of the test adhesive film. MVTR was calculated as the weight loss per time divided by the area of the opening in the cup (g/m$^2$/24 h).

The MVTR of a material is a linear function of the thickness of the material. Thus, when reporting MVTR to characterize a material, it is important to inform the thickness of the material which MVTR was reported. We used 150 µm as a reference. If thinner or thicker samples were measured, the MVTR was reported as corresponding to a 150 µm sample. Thus a 300 µm sample with a measured MVTR of 10 g/m$^2$/24 h was reported as having MVTR=20 g/m$^2$/24 h for a 150 µm sample because of the linear connection between thickness of sample and MVTR of sample.

Finally, we noted that by using this method, we introduced an error by using a supporting PU film. Utilizing the fact that the adhesive/film laminate was a system of two resistances in series eliminated the error. When the film and the adhesive are homogeneous, the transmission rate may be expressed as:

$$1/P(\text{measured})=1/P(\text{film})+1/P(\text{adhesive}).$$

Hence, by knowing the film permeability and thickness of the adhesive, it was possible to calculate the true permeability of the adhesive, P(adhesive), using the following expression:

$$P(\text{adhesive})=d(\text{adhesive})/150\ \mu\text{m}*1/(1/P(\text{measured})-1/P(\text{film}))$$

where d(adhesive) was the actual measured thickness of the adhesive and P(film) was the MVTR of the film without any adhesive on and P(measured) was the actual measured MVTR.

Moisture Absorption

Samples were prepared by thermoforming to a 0.5 mm thick adhesive film between two release liners. With a punching tool, samples were punched out. Sample size was 25×25 mm. The release liners were removed. The samples were glued to an object glass and placed in a beaker with physiological salt water and placed in an incubator at 37° C.

The sample was weighed at the outset (M(start)) and after 2 hours (M(2 hours). Before weighing, the object glass was dried off with a cloth. For a 25×25 mm sample the area was 6.25 cm$^2$ (the surface edges were left out of the area). The moisture absorption may be calculated as: Water absorption after 2 hours=(M(2 hours)−M(start))/6.25 cm$^2$. The result is in the unit g/cm$^2$ per 2 hours.

Peel Test

Substrate for Peel Test and Liquid Media.

The substrate used to simulate real use is skin.

The peel liquid media is a 4% hand soap solution in saline.

Peel Setup

In order to simulate a leakage propagation in a peel measurement, a low and constant peel angle is chosen. This peel setup has a constant peel of 40 degrees and constant peel load of 500 g. The peel extension is measured with time. Different dwell times (time from applying the adhesive to the skin until test start) are used in order to observe the instant adhesion properties of a second adhesive as well as a switchable adhesive as described herein. Peel experiments are done at ambient temperature, approximately 20° C.

DETAILED DESCRIPTION OF THE DRAWINGS

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Embodiments, and features of the various exemplary embodiments described in this application, may be combined with each other ("mixed and matched"), unless specifically noted otherwise.

In FIG. 1 is shown a cross-section of an adhesive wafer for an ostomy device. For simplicity, collection bag and/or coupling for attaching such bags have been omitted in the drawing. The wafer comprises a backing layer 1 coated on the skin-facing surface with a second adhesive 3. A first switchable adhesive 2 is provided at the central portion of the wafer, surrounding a through-going hole 5 for accommodating a stoma. A release liner 4 is covering the skin-facing surface of the wafer before application. The release liner 4 is provided with a form stable recess for containing the first adhesive 2.

Figure 2:
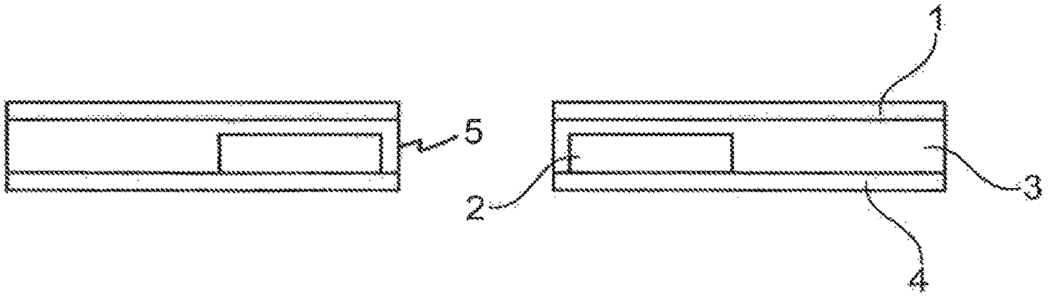
FIG. 2 shows another embodiment in cross-section.

FIG. 2 is a cross-section of shown a wafer comprising a backing layer 1 being coated on the skin-facing surface with a second adhesive 3. A first switchable adhesive 2 is provided at the central portion of the wafer, surrounding a through-going hole 5 for accommodating a stoma. A release liner 4 is covering the skin-facing surface of the wafer before application. The central portion of the second adhesive 3 is provided with a recess for containing the first adhesive 2. The skin-facing surface of the wafer is substantially planar.

Figure 3:
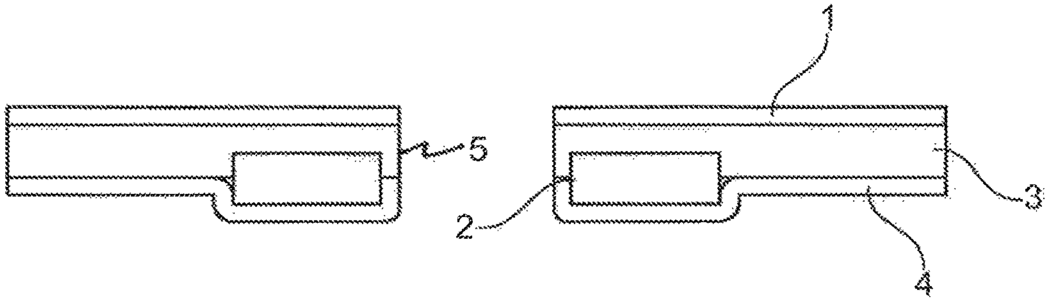
FIG. 3 shows yet an embodiment of in cross-section.

In FIG. 3 is a cross-section of shown a wafer where the both the second adhesive 3 and the release liner 4 are provided with a recess for containing the first adhesive 2.

Figure 4:
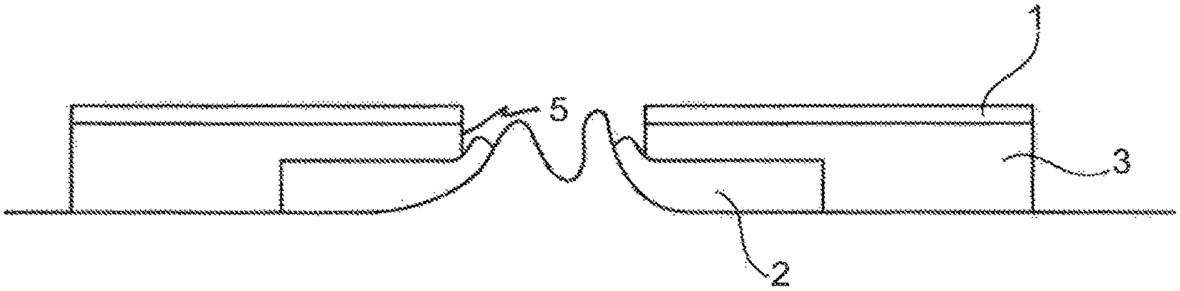
FIG. 4 shows the embodiment of FIG. 2 applied to the skin surrounding a stoma

In FIG. 4 is shown a cross-section of a wafer applied to the skin surrounding a stoma. The release liner is removed and the first adhesive 2 has been molded to fit around the stoma.

Figure 5:
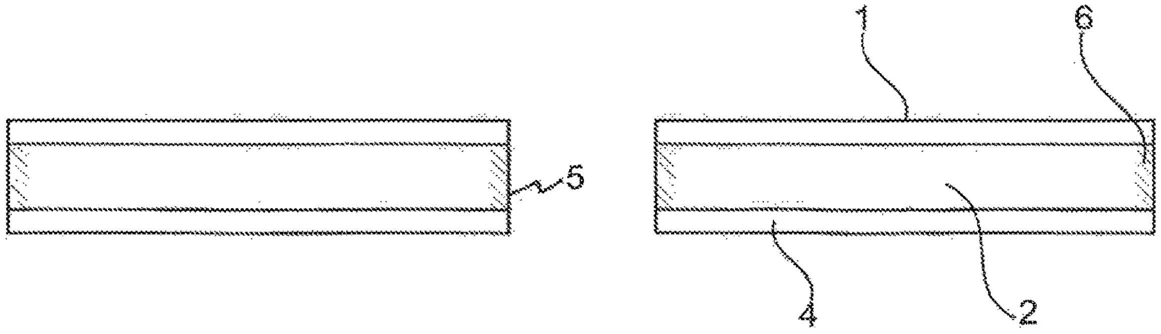
FIG. 5 shows an embodiment in cross-section.

In FIG. 5 is shown an embodiment with a backing layer 1, a first switchable adhesive layer 2 and a release liner 4. Along the edge portions 6, the adhesive has been switched into a more form stable texture, thereby preventing the adhesive to flow out of the wafer.

Figure 6:
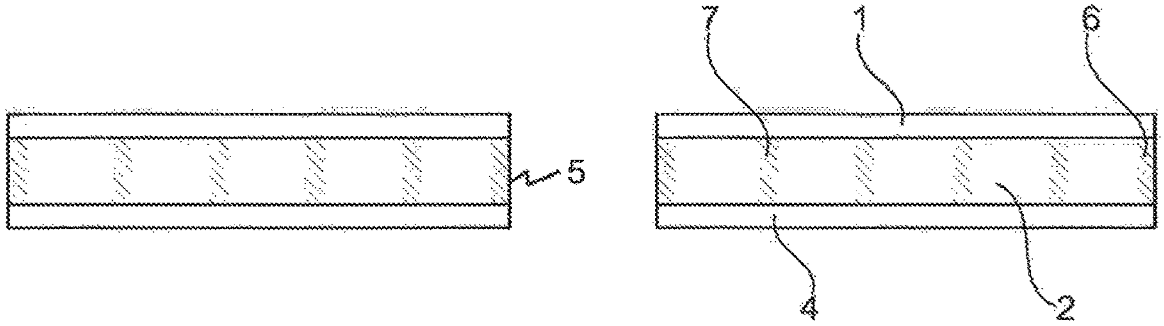
FIG. 6 shows an embodiment in cross-section and FIG. 7 shows an embodiment in cross-section.

In FIG. 6 is shown an embodiment with a backing layer 1, a first switchable adhesive layer 2 and a release liner 4. Along the edge portions 6, and at points 7 in the central portion of the first adhesive layer, the adhesive has been switched into a more form stable texture, thereby preventing the adhesive to flow out of the wafer. The switched points or lines 7 in the centre may divide the adhesive 2 into smaller compartments.

Figure 7:
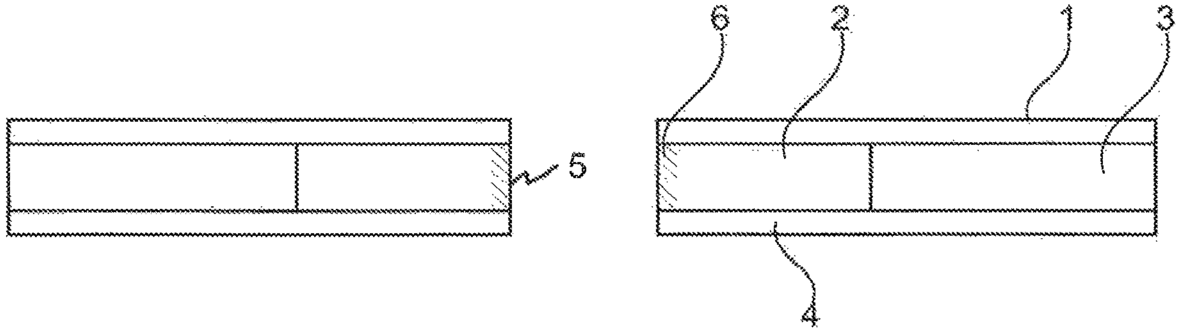

In FIG. 7 is shown an embodiment with a backing layer 1, a first switchable adhesive layer 2 at the central portion of the wafer and second adhesive 3 at the peripheral portion of the wafer and a release liner 4. Along the edge portions 6, the adhesive 2 has been switched into a more form stable texture, thereby preventing the adhesive 2 to flow out of the wafer.

EXAMPLES

Sample 1

An Adhesive Wafer with Full Cover of Switchable Adhesive

The adhesive wafer consist of a backing layer (DOW Saranex 630G), coated with a switchable adhesive (Composition: 74% BASF acResin A 260 UV with 1% photoinitiator* and 25% hydrocolloids**) with a thickness of 1 mm and a round geometry of 110 mm, and a siliconiced release liner (0.11 mm PPB, 1803 from Hutamaki).

*Photoinitiator chemistry: Irgacure 784 photoinitiator from Ciba, Bis(.eta.5-2,4-cylcopentadien-1-yl)-bis(2,6-difluoro-3-(1H-pyrrol-1-yl)-phenyl) titanium).

**Hydrocolloid mixture: 25% hydrocolloids, (10% (w/w) pectin LM CG, CP Kelco, 20% (w/w) Akucell AF288, Akzo Nobel, 30% (w/w) PB gelatine, PB Gelatins and 40% (w/w) Guar gum FG-20, Hercules Corp.).

The wafer is intended to have paste like properties and changed adhesion characteristics from a moldable paste texture to a form stable adhesive texture when switched.

Sample 2

An Adhesive Wafer with Switchable Adhesive at the Central Portion

The adhesive wafer consist of a backing layer (DOW Saranex 630G), a full cover adhesive based on a standard hyderocolloide adhesive*** with a thickness of 1 mm and a round geometry of 110 mm, a switchable adhesive (Composition: 74% BASF acResin A 260 UV with 1% photoinitiator* and 25% hydrocolloids) of 2 mm thickness at the central portion and a round geometry with a diameter of 70 mm and a siliconiced release liner (0.11 mm PPB, 1803 from Hutamaki). A second adhesive* is provided at the peripheral portion and over the distal portion of the switchable adhesive.

***((10% (w/w) Kraton 1161, from Kraton polymers, 40% Ooppanol B12 from BASF 5% (w/w) pectin LM CG, CP Kelco, 10% (w/w) Akucell AF288, Akzo Nobel, 15% (w/w) PB gelatine, PB Gelatins and 20% (w/w) Guar gum FG-20, Hercules Corp). the components are mixed for 20 min in a z blade Austin 300 g mixer for 20 min).

The first adhesive was intended to have paste like properties and will change adhesion characteristics from moldable paste texture to a form stable adhesive texture when switched. The peripheral adhesive will not change state.

The samples were applied to skin the adhesive properties investigated by a peel test. As can be seen from Table 1, the switchable adhesive separates during peel when it is not switched, in a cohesive break (the adhesive is ruptured and residues remain on both the wafer and the skin.

TABLE 1

| | Adhesion properties: | |
|---|---|---|
| | Fracture type when removed from skin**** Before switching the adhesive | Fracture type when removed from skin**** After switching the adhesive |
| Example 1 | Cohesive break in paste | Adhesive break |
| Example 2 | Cohesive break in paste (center), Adhesive break (rim) | Adhesive break (center), Adhesive break (rim) |

****Adhesives stays on skin 10 min before removal.

As an alternative examples of a switchable adhesive, a moisture-switchable adhesive could be used. A moisture-switchable adhesive could, for instance, be one of the following:

Moisture Composition 12: Mixed Moisture-Switchable Silicone Adhesive with 10% Mixed Hydrocolloids Trio Silken (18 g, 36 wt %, Trio Healthcare) was mixed with a mixture of hydrocolloids (5 g, 10 wt %) using Speedmixer at 3000 rpm for 3 minutes. The hydrocolloid mixture consists of carboxymethyl cellulose (20 wt %), guar gum (40 wt %), gelatin (30 wt %) and pectin (10 wt %). An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a polyurethane Biatain film (30 μm) using an applicator. For the switch experiments, this composition was switched in either an oven at 32° C., or in a humidity cupboard (Binder KBF) at 32° C. and 50% relative humidity.

Viscosity measured before switch: 351 Pa s at 0.01 Hz.

Moisture Composition 17: Mixed Moisture-Switchable Silicone Adhesive with 40% Dried Mixed Hydrocolloids Trio Silken (12 g, 24 wt %, Trio Healthcare) was mixed with a mixture of hydrocolloids (20 g, 40 wt %) using Speedmixer at 3000 rpm for 3 minutes. The hydrocolloid mixture consists of carboxymethyl cellulose (20 wt %, Akucell AF 2881, Akzo Nobel), guar gum (40 wt %, guar gum FG-200, Nordisk Gelatine), gelatin (30 wt %, gelatin UF220, PB Gelatins GmbH) and pectin (10 wt %, LM 12 CG-Z/200, CP Kelco). The hydrocolloids were dried at 80° C. before being added to the formulation until they reached a water content of 2.43 wt %. An unreactive silicone polymer, BioPSA (18 g, 36 wt %, Dow Corning 7-4560) was added to the mixture, and the mixture was mixed using Speedmixer for additional 3 minutes at 3000 rpm. The resulting mixture was coated on a film using an applicator, and the film was cured in an oven at 32° C. with a relative humidity of 50% before testing.

Viscosity measured before switch: 2366 Pa s at 0.01 Hz.

The invention claimed is:

1. An adhesive wafer adapted to attach a waste collecting bag to a skin surface of a user, the adhesive wafer comprising:

a backing layer;

an adhesive composition disposed on the backing layer;

a first switchable adhesive composition in contact with the adhesive composition and in contact with the backing layer, where the first switchable adhesive composition is flowable and contained in a recess of the adhesive wafer; and a release liner covering the adhesive composition and the first switchable adhesive composition;

wherein the first switchable adhesive composition comprises a polymer and a switch initiator, and the first switchable adhesive composition is adapted to be switched from a first liquid state to a second adhesive state by transmission of light through the backing layer for activation of the switch initiator;

wherein the first switchable adhesive composition has a higher viscosity in the second adhesive state than in the first liquid state;

wherein peel force increases from the first liquid state to the second adhesive state; and wherein the second adhesive state has a second repeated peel force above 1 N.

2. The adhesive wafer of claim 1, wherein the recess is provided by an edge portion of the first switchable adhesive composition after the first switchable adhesive composition has been activated by the switch initiator into a form-stable texture of the second adhesive state.

3. The adhesive wafer of claim 1, further comprising a through-going hole formed through the backing layer and the adhesive composition.

4. The adhesive wafer of claim 3, wherein the first switchable adhesive composition has an inner rim that is spaced a radial distance away from the through-going hole.

5. The adhesive wafer of claim 1, wherein the recess is formed in the release liner.

6. The adhesive wafer of claim 1, wherein the recess is formed in the adhesive composition and in the release liner.

7. The adhesive wafer of claim 1, wherein the recess is formed in the adhesive composition.

8. The adhesive wafer of claim 1, wherein the adhesive composition and the first switchable adhesive composition are co-planar in a single plane of the release liner.

9. The adhesive wafer of claim 1, wherein the release liner is in contact with both the adhesive composition and the first switchable adhesive composition.

10. The adhesive wafer of claim 1, wherein the adhesive composition is located at an outermost peripheral edge of the adhesive wafer.

11. The adhesive wafer of claim 1, wherein the adhesive wafer has a peripheral ring surrounding a central part, with a stoma receiving through-going hole formed through the central part of the adhesive wafer, and the first switchable adhesive composition is located only in the central part of the adhesive wafer.

12. The adhesive wafer of claim 1, wherein the first switchable adhesive composition in the first liquid state has a complex viscosity below 0.4 mega-Pascal-seconds and in the second adhesive state a higher complex viscosity than the complex viscosity of the first liquid state.

13. A method of applying an ostomy device to an ostomate, the method comprising:

providing an adhesive wafer comprising a backing layer, an adhesive composition disposed on the backing layer, a first switchable adhesive composition in contact with the adhesive composition, where the first switchable adhesive composition is flowable and contained in a recess of the adhesive wafer, and a release liner covering the adhesive composition and the first switchable adhesive composition;

removing the release liner from the adhesive composition and the first switchable adhesive composition;

applying the adhesive wafer to skin around a stoma;

pressing the first switchable adhesive composition into contact with the stoma; and activating a switch initiator in the first switchable adhesive composition by passing light through the backing layer and switching the first switchable adhesive composition from a liquid state to an adhesive state, wherein peel force increases from the liquid state to the adhesive state; and wherein the second adhesive state has a second repeated peel force above 1 N.

* * * * *

UNITED STATES PATENT AND TRADEMARK OFFICE

CERTIFICATE OF CORRECTION

PATENT NO. : 11,160,681 B2
APPLICATION NO. : 15/565448
DATED : November 2, 2021
INVENTOR(S) : Strøbech et al.

It is certified that error appears in the above-identified patent and that said Letters Patent is hereby corrected as shown below:

In the Specification

In Column 4, Line 32, delete "exists" and insert -- exist --, therefor.

In Column 5, Line 26, delete "10 second," and insert -- 10 seconds, --, therefor.

In Column 10, Line 35, delete "an crosslinker" and insert -- a crosslinker --, therefor.

In Column 16, Line 48, delete "10" and insert -- $|\eta^*|$ --, therefor.

In Column 19, Line 19, delete "siliconiced" and insert -- siliconized --, therefor.

In Column 19, Line 33, delete "hyderocolloide" and insert -- hydrocolloid --, therefor.

In Column 19, Line 38, delete "siliconiced" and insert -- siliconized --, therefor.

In Column 20, Line 1, delete "examples" and insert -- example --, therefor.

In the Claims

In Column 22, Line 27, in Claim 13, delete "wherein the second adhesive state" and insert -- wherein the adhesive state --, therefor.

Signed and Sealed this
Twenty-eighth Day of June, 2022

Katherine Kelly Vidal

Katherine Kelly Vidal
*Director of the United States Patent and Trademark Office*